United States Patent [19]
Dedrick et al.

[11] Patent Number: 5,990,082
[45] Date of Patent: *Nov. 23, 1999

[54] USES OF LIPOPOLYSACCHARIDE BINDING PROTEIN

[75] Inventors: Russell L. Dedrick, Kensington; Stephen F. Carroll, Walnut Creek, both of Calif.

[73] Assignee: Xoma Corporation, Berkeley, Calif.

[ * ] Notice: This patent issued on a continued prosecution application filed under 37 CFR 1.53(d), and is subject to the twenty year patent term provisions of 35 U.S.C. 154(a)(2).

[21] Appl. No.: 08/955,660

[22] Filed: Oct. 22, 1997

[51] Int. Cl.$^6$ .......................... A61K 38/00; A61K 38/16
[52] U.S. Cl. .................................. 514/8; 514/2; 435/68.1
[58] Field of Search ........................... 514/2, 8; 435/68.1

[56] References Cited

U.S. PATENT DOCUMENTS

| | | | |
|---|---|---|---|
| 5,245,013 | 9/1993 | Ulevitch et al. | 530/380 |
| 5,310,879 | 5/1994 | Ulevitch et al. | 530/388.1 |
| 5,484,705 | 1/1996 | White et al. | 435/7.32 |
| 5,488,034 | 1/1996 | McGregor et al. | 514/12 |
| 5,696,090 | 12/1997 | McGregor et al. | 514/12 |
| 5,731,415 | 3/1998 | Gazzano-Santoro | 530/350 |
| 5,770,561 | 6/1998 | Horwitz | 514/8 |
| 5,804,367 | 9/1998 | White et al. | 435/4 |

FOREIGN PATENT DOCUMENTS

| | | |
|---|---|---|
| WO 86/06279 | 11/1986 | WIPO . |
| WO 91/01639 | 2/1991 | WIPO . |
| WO 92/03535 | 3/1992 | WIPO . |
| WO 93/05797 | 4/1993 | WIPO . |
| WO 93/06228 | 4/1993 | WIPO . |
| WO 94/17819 | 8/1994 | WIPO . |
| WO 94/21280 | 9/1994 | WIPO . |
| WO 94/25476 | 11/1994 | WIPO . |
| WO 95/00641 | 1/1995 | WIPO . |
| WO 95/02414 | 1/1995 | WIPO . |
| WO 95/20163 | 7/1995 | WIPO . |
| WO 96/21436 | 7/1996 | WIPO . |

OTHER PUBLICATIONS

Elevated levels of lipopolysaccharide (LPS) binding protein (LBP) reduce the inflammatory potential of LPS in vitro and in vivo. Fourth International Endotoxin Society Conference, Nagoya, Japan, Oct. 22–25, 1996. Journal of Endotoxin Resear.

Abrahamson, S.L., et al., "Biochemical Characterization of Recombinant Fusions of Lipopolysaccharide Binding Protein and Bactericidal/Permeability–increasing Protein," *J. Biological Chemistry*, 272(4):2149–2155 (Jan., 1997).

Beekhuizen, H. et al., "CD14 Contributes to the Adherence of Human Monocytes to Cytokine–Stimulated Endothelial Cells," *J. Immunology*, 147(11):3761–3767 (Dec., 1991).

Bone, R.C. "The Pathogenesis of Sepsis," *Annals Internal Medicine*, 115:457–469 (1991).

Corradin, S.B. et al., "Enhancement of murine macrophage binding of and response to bacterial lipopolysaccharide (LPS) by LPS–binding protein," *J. Leukocyte Biology*, 52:363–368 (Oct., 1992).

de Winter, R.J. et al., "Recombinant Endotoxin–Binding Protein (rBPI$_{23}$) Attenuates Endotoxin–Induced Circulatory Changes in Humans," *J. Inflammation*, 45: 193–206 (1995).

Dedrick, R.L. et al., "Elevated Levels of Lipopolysaccharide (LPS) Binding Protein (LBP) Reduce the Inflammatory Potential of LPS in Vitro and in Vivo," *J. Endotoxin Research*, 3(supp. 1):18 (Abstract I–14) (Oct., 1996).

Dubin, W. et al., "Asthma and endotoxin: lipopolysaccharide–binding protein and soluble CD14 in bronchoalveolar compartment," *Am. J. Physiol.*, 270:L736–L744 (1996).

Frey, E.A. et al., "Soluble CD14 Participates in the Response of Cells to Lipopolysaccharide," *J. Exp. MEd.*, 176:1665–1671 (Dec., 1992).

Froon, A.H.M., et al., "Lipopolysaccharide Toxicity–Regulating Proteins in Bacteremia," *J. Infectious Diseases*, 171:1250–1257 (1995).

Gallay, P. et al., "Purification and Characterization of Murine Lipopolysaccharide–Binding Protein," *Infection and Immunity*, 61(2):378–383 (Feb., 1993).

Gazzano–Santoro, H. et al., "Competition between rBPI$_{23}$, a Recombinant Fragment of Bactericidal/Permeability–Increasing Protein, and Lipopolysaccharide (LPS)–Binding Protein for Binding to LPS and Gram–Negative Bacteria," *Infection Immunity*, 62(4): 1185–1191 (Apr., 1994).

Gegner, J.A. et al., "Lipopolysaccharide (LPS) Signal Transduction and Clearance," *J. Biological Chemistry*, 270(10): 5320–5235 (Mar., 1995).

Geller, D.A., et al., "Induction of Hepatocyte Lipopolysaccharide Binding Protein in Models of Sepsis and the Acute–Phase Response," *Arch. Surg.*, 128(1): 22–28 (Jan., 1993).

Hailman, E. et al., "Lipopolysaccharide (LPS)–binding Protein Accelerates the Binding of LPS to CD14," *J. Exp. Med.*, 179(1): 269–277 (Jan., 1994).

Han, J. et al., "Lipopolysaccharide (LPS) Binding Protein, Truncated at the Ile–197, Binds LPS but does not Transfer LPS to CD14," *J. Biological Chemistry*, 269(11): 8172–8175 (Mar., 1994).

Haziot, A. et al., "Recombinant Soluble CD14 Prevents Mortality in Mice Treated with Endotoxin (Lipopolysaccharide)," *J. Immunology*, 154: 6529–6532 (1995).

Haziot, A. et al., "Recombinant Soluble CD14 Inhibits LPS–Induced Tumor Necrosis Factor–α Production by Cells in Whole Blood," *J. Immunology*, 152: 5868–5876 (1994).

(List continued on next page.)

*Primary Examiner*—Cecilia J. Tsang
*Assistant Examiner*—Michael Borin
*Attorney, Agent, or Firm*—Marshall, O'Toole, Gerstein, Murray & Borun

[57] ABSTRACT

Novel LBP compositions and therapeutic uses for LBP are provided for preventing the adverse effects of exposure to endotoxin.

3 Claims, 7 Drawing Sheets

OTHER PUBLICATIONS

Heumann, D. et al., "Competition between Bacterial/Permeability–Increasing Protein and Lipopolysaccharide–Binding Protein for Lipopolysaccharide Binding to Monocytes," *J. Infectious Diseases*, 167: 1351–1357 (1993).

Heumann, D. et al., "Radioimmunoassay versus flow cytometric assay to quantify LPS–binding protein (LBP) concentrations in human plasma," *J. Immunological Methods*, 171:169–176 (1994).

Huang, K. et al., "Lipopolysaccharide–Induced E–Selectin Expression Requires Continuous Presence of LPS and is Inhibited by Bactericidal/Permeability–Increasing Protein," *Inflammation*, 19(3):389–404 (1995).

Iriye, B.K. et al., "Differences in the Concentration of an Endotoxin Binding Protein Help Explain Sensitivity to Septic Complications in Pregnancy," *Am. J. Obstetrics Gynecol.*, 174(1 pt. 2):390 (1996) (Abstract 291).

Kirkland, T.N. et al., "Analysis of Lipopolysaccharide Binding by CD14," *J. Biological Chemistry*, 268(33): 24818–24823 (Nov., 1993).

Lee, J–D et al., "Transfection of CD14 into 70Z/3 Cells Dramatically Enhances the Sensitivity to Complexes of Lipopolysaccharides (LPS) and LPS Binding Protein," *J. Experimental Medicine*, 175:1697–1705 (Jun., 1992).

Leturcq, D. et al, "Generation of Monoclonal Antibodies to Human LBP and Their Use in the Detection of LBP Protein in Serum", *J. Cell. Biochem.*, 16C:161 (1992) (Abstract CB 109).

Little, D. et al., "Perioperative immune modulation," *Surgery*, 114(1): 87–91 (1993).

Marra, M.N. et al., "The Role of Bactericidal/Permeability—Increasing Protein as a Natural Inhibitor of Bacterial Endotoxin," *J. Immunology*, 148(2):532–537 (Jan., 1992).

Marra, M.N. et al., "Bactericidal/Permeability—Increasing Protein has Endotoxin–Neutralizing Activity," *J. Immunology*, 144(2): 662–666 (1990).

Mathison, J.C. et al., "Plasma Lipopolysaccharide (LPS-)–Binding Protein," *J. Immunology*, 149(1):200–206 (Jul. 1, 1992).

Mathison, J. et al., "Regulatory Mechanisms of Host Responsiveness to Endotoxin (Lipopolysaccharide)," *Pathobiology*, 59:185–188 (1991).

Mészáros, K. et al., "Immunoreactivity and Bioactivity of Lipopolysaccharide–Binding Protein in Normal and Heat–Inactivated Sera," *Infection and Immunity*, 63(1): 363–366 (Jan., 1995).

Morrison, D.C. et al., "The Effects of Bacterial Endotoxins on Host Mediation Systems," *Am. J. Pathology*, 93(2):527–618 (Nov., 1978).

Ooi et al., "Endotoxin–Neutralizing Properties of the 25 kD N–Terminal Fragment and a Newly Isolated 30kD C–Terminal Fragment of the 55–60 kD Bactericidal/Permeability–increasing Protein of Human Neutrophils," *J. Exp. Med.*, 174:649–655 (Sep., 1991).

Opal, S.M. et al., "Activity of Lipopolysaccharide–Binding Protein–Bactericidal/Permeability–Increasing Protein Fusion Peptide in an Experimental Model of Pseudomonas Sepsis," *Antimicrobial Agents Chemotherapy*, 39(12): 2813–2815 (Dec., 1995).

Pugin, J. et al., "Lipopolysaccharide activation of human endothelial and epithelial cells is mediated by lipopolysaccharide–binding protein and soluble CD14," *Proc. Natl. Acad. Sci., USA*, 90:2744–2748 (Apr., 1993).

Pugin, J. et al., "Soluble CD14 and Lipopolysaccharide Binding Protein Mediate Epithelial Cell Responses to Lipopolysaccharides," *FASEB J.*, A142 (Abstract 824) (1993).

Schindler, R. et al., "Plasma levels of bactericidal/permeability–increasing protein (BPI) and lipopolysaccharide-–binding protein (LBP) during hemodialysis," *Clinical Nephrology*, 40(6):346–351 (1993).

Schumann, R.R. et al., "Significantly Elevated Levels of Lipopolysaccharide Binding Protein (LBP) in Patients with Severe Sepsis: A Prospective Cohort Study with 109 surgical ICU Patients," 36th Int'l Conf. on Antimicrobial Agents and Chemotherapy, New Orleans, LA, Sep. 15–18, (1996) (Abstract LB17).

Schumann et al., "Structure and Function of Lipopolysaccharide Binding Protein", *Science*, 249:1429–1431 (Sep., 1990).

Schütt, C. et al., "CD14 Prevents Endotoxin Inducible Oxidative Burst Response of Human Monocytes," *Allerg. Immunol.*, 37: 159–164 (1991).

Schütt, C. et al., "Endotoxin–neutralizing capacity of soluble CD14," *Res. Immunol.*, 143: 71–78 (1992).

Taylor, A.H. et al., "Lipopolysaccharide (LPS) Neutralizing Peptides Reveal a Lipid A Binding Site of LPS Binding Protein," *J. Biological Chemistry*, 270(30): 17934–17938 (Jul., 1995).

Theofan et al., "An Amino–Terminal Fragment of Human Lipopolysaccharide–Binding Protein Retains Lipid A Binding but Not CD14–Stimulatory Activity", *J. Immunology*, 152(7): 3623–3629 (1994).

Tobias, P.S. et al., "Identification of a Lipid A Binding Site in the Acute Phase Reactant Lipopolysaccharide Binding Protein," *J. Biological Chemistry*, 264(18):10867–10871 (Jun., 1989).

Tobias, P.S. et al., "A Family of Lipopolysaccharide Binding Proteins Involoved in Responses to Gram–negative Sepsis," *J. Biological Chemistry*, 263(27):13479–13481 (Sep., 1988).

Tobias, P.S. et al., "Lipopolysaccharide Binding Protein-–mediated Complexation of Lipopolysaccharide with Soluble CD14," *J. Biological Chemistry*, 270(18):10482–10488 (May, 1995).

Tobias, P.S. et al., "Lipopolysaccharide Binding Protein," *J. Cell. Biochem.*, 16C:151 (Abstract CB006) (1992).

Tobias, S. et al., "Control of Lipopolysaccharide–High Density Lipoprotein Binding by Acute Phase Protein(s)," *J. Immunology*, 131(4): 1913–1916 (Oct., 1983).

Tobias, P.S. et al., "Control of Lipopolysaccharide–High-–Density Lipoprotein Interactions by an Acute–Phase Reactant in Human Serum," *Infection Immunity, (United States)*, 50 (1): 73–76 (Oct., 1985).

Tobias, P.S. et al., "Isolation of a Lipopolysaccharide–Binding Acute Phase Reactant from Rabbit Serum," *J. Exp. Med.*, 164:777–793 (Sep., 1986).

Tobias, P.S. et al., "Participation of Lipopolysaccharide-–binding Protein in Lipopolysaccharide–dependent Marcophage Activation," *Am. J. Resp. Cell. Mol. Biol.*, 7:239–245 (1992).

Tracey, K.J. et al., "The Role of Cytokine Mediators in Septik Shock," *Adv. Surg.*, 23: 21–56 (1990).

Ulevitch, R.J. et al., "The Modification of Biophysical and Endotoxic Properties of Bacterial Lipopolysaccharides by Serum," *J. Clin. Invest. (United States)*, 62(6): 1313–1324 (Dec., 1978).

Wilde, C.G. et al., "Bactericidal/Permeability–increasing Protein and Lipopolysaccharide (LPS)–binding Protein," *J. Biological Chemistry*, 269(26): 17411–17416 (Jul., 1994).

Worthen, G.S. et al., "Neutrophil Adherence Induced by Lipopolysaccharide in Vitro," *J. Clin. Invest.*, 90:2526–2535 (Dec., 1992).

Wright, S.D. et al., "CD14, a Receptor for Complexes of Lipopolysaccharide (LPS) and LPS Binding Protein", *Science*, 249:1431–1433 (Sep., 1990).

Wright, S.D. et al., "Activation of the Adhesive Capacity of CR3 on Neutrophils by Endotoxin: Dependence on Lipopolysaccharide Binding Protein and CD14," *J. Exp. Med.*, 173(5): 1281–1286 (May, 1991).

Wright, S.D. et al., "Lipopolysaccharide (LPS) Binding Protein Opsonizes LPS–Bearing Particles for Recognition by a Novel Receptor on Macrophages," *J. Exp. Med.*, 170(4): 1231–1241 (Oct., 1989).

Wurfel, M.M. et al., "Lipopolysaccharide (LPS)–binding Protein Is Carried on Lipoproteins and Acts as a Cofactor in the Neutralization of LPS," *J. Exp. Med.*, 180: 1025–1035 (Sep., 1994).

Yu, B. et al., "Catalytic Properties of Lipopolysaccharide (LPS) Binding Protein," *J. Biological Chemistry*, 271(8): 4110–4105 (Feb., 1996).

LPS-Induced TNF Expression in Serum Free Medium

LPS-Induced TNF Expression in RPMI with 10% FBS

LPS-Induced E-Selectin Expression in HUVEC

IL-1β-Induced E-Selectin Expression in HUVEC 15 mg/kg LPS ± rLBP 20 mg/kg LPS ± rLBP 25 mg/kg LPS ± rLBP

USES OF LIPOPOLYSACCHARIDE BINDING PROTEIN

The present invention relates to a novel use of lipopolysaccharide binding protein (LBP) as a prophylactic/therapeutic agent in blocking the pathological effects of lipopolysaccharide (LPS), also known as endotoxin.

BACKGROUND OF THE INVENTION

LPS is a major component of the outer membrane of gram-negative bacteria and consists of serotype-specific O-side chain polysaccharides linked to a conserved region of core oligosaccharide and lipid A. LPS is a potent inducer of inflammation, stimulating the expression of many pro-inflammatory and pro-coagulant mediators in monocytes, macrophages and endothelial cells. These responses are important in containing and eliminating a localized infection, however, adverse effects of systemic exposure to LPS can include induction of an inflammatory cascade, damage to endothelium, widespread coagulopathies, and organ damage. Systemic exposure to LPS can arise from direct infection of gram negative bacteria, leading to the complications of gram-negative sepsis [Tracey et al., *Adv. Surg.* 23: 21–56 (1990)]. Alternatively, a variety of conditions and circumstances, including trauma, can induce changes in gut permeability that result in translocation of bacteria, and therefore LPS, into circulating blood. Bacterial LPS translocated from the gut is thought to play a major role in post-surgical immunosuppression [Little et al., *Surgery* 114(1): 87–91 (1993)] and hemorrhagic shock. Therefore, there exists a need to discover therapies that can counteract the effects of LPS in pathologic situations.

Two proteins, CD14 and lipopolysaccharide binding protein (LBP) [Schumann et al., *Science* 249: 1429–1431 (1990); Wright et al., *Science* 249: 1431–1433 (1990)] have been shown to be required to generate an inflammatory response to LPS. LPS must bind to CD14 to activate an inflammatory response. CD14 is a 55 kD protein expressed via a glycosylphosphatidylinositol-anchor on the surface of macrophages, monocytes and neutrophils (mCD14). Endothelial and epithelial cells, which do not express the CD14 protein, are activated by LPS bound to a soluble form of (sCD14) found in serum or plasma (at a concentration of about 2 $\mu$g/mL in normal human blood). CD14 preferentially binds to LPS monomers [Tobias et al., *J. Biol. Chem.* 270(18): 10482–10488 (1995)]. Since purified LPS exists in aqueous solution in micelles or aggregates, direct binding of LPS to CD14 is very slow [Tobias et al. (1995), supra; Yu and Wright, *J. Biol. Chem.* 271(8): 4110–4105 (1996)] and only occurs at high concentrations of LPS [Hailman et al., *J. Exp. Med.* 179(1): 269–277 (1994)]. Binding of LPS to CD14 is greatly accelerated by LBP [Hailman et al. (1994), supra; Tobias et al. (1995), supra; Yu et al. (1996), supra], and LBP is required for activation of cells by either mCD14 or sCD14 at physiological concentrations of LPS [Schumann et al. (1990), supra; Wright et al. (1990), supra].

LBP is a 60 kD glycoprotein synthesized in the liver and present in normal human serum. LBP belongs to the group of plasma proteins called acute phase proteins, including C-reactive protein, fibrinogen and serum amyloid A, that increase in concentration in response to infectious, inflammatory and toxic mediators. LBP expression has been induced in animals by challenge with LPS, silver nitrate, turpentine and Corynebacterium parvum [Geller et al., *Arch. Surg.* 128(1): 22–28 (1993); Gallay et al., *Infect. Immun.* 61(2): 378–383 (1993); Tobias et al., *J. Exp. Med.* 164: 777–793 (1986)]. However, while administration of silver nitrate caused LBP levels to increase in several strains of mice, this was not observed in one strain, C3H/HeJ, in which LPS does not induce an inflammatory response [Gallay et al. (1993), supra]. Recently, an analysis of different human disease states has indicated that increased LBP levels are uniquely correlated with exposure to LPS. In human patients with presumed gram-negative sepsis, serum LBP levels can reach from about 50 to about 100 $\mu$g/mL [U.S. Pat. No. 5,484,705]. In contrast, in other disease states, such as rheumatoid arthritis, involving an acute phase response in which elevated levels of the acute phase proteins CRP and fibrinogen were measured in patient serum samples, no significant increases in LBP levels were observed. Elevated, particularly persistently elevated, LBP levels have been correlated with poor clinical outcome in septic patients [U.S. Pat. No. 5,484,705, and U.S. Ser. No. 08/377,391 filed Jan. 24, 1995, now U.S. Pat. No. 5,804,367, both of which are hereby incorporated by reference in their entirety. This has been confirmed by Schumann et al., 36th Int'l Conf. on Antimicrobial Agents and Chemotherapy, New Orleans, La., Sep. 15–18, 1996.

LBP is reported to bind to LPS aggregates (at low LBP to LPS ratios) or to disaggregate LPS vesicles (at high LBP to LPS ratios) [Tobias et al. (1995), supra] to form an LBP:LPS complex that greatly facilitates binding of LPS to either mCD14 or sCD14 [Wright et al., *J. Exp. Med.* 173(5): 1281–1286 (1991); Hailman et al. (1994), supra; Yu et al. (1996), supra; Tobias et al. (1995), supra]. LBP is reported to act catalytically in facilitating LPS binding to CD14, a single LBP molecule enabling the transfer over 100 LPS molecules to CD14 [Hailman et al. (1994), supra]. LBP is also reported to remain associated with LPS aggregates or LPS coated particles and facilitate binding to cells expressing mCD14 in a phenomenon known as opsonization [Wright et al., *J. Exp. Med.* 170(4): 1231–1241 (1989); Kirkland et al., *J. Biol. Chem.* 268(33): 24818–24823 (1993); Gegner et al., *J. Biol. Chem.* 270(10): 5320–5325 (1995)]. Thus, LBP potentiates the inflammatory activity of LPS and is recognized as an immunostimulatory molecule. Functional analysis of the LBP molecule has demonstrated that LPS binding resides in the approximate N-terminal half of the protein, but the C-terminal half is required to permit transfer of LPS to CD14 [U.S. application Ser. No. 08/261, 660 filed Jun. 17, 1994 now U.S. Pat. No. 5,731,415, Theofan et al., *J. Immunol.* 152(7): 3624–3629 (1994); Han et al., *J. Biol. Chem.* 269(11): 8172–8175 (1994)]. Because of the observed potentiating effect LBP has on the inflammatory potential of LPS, blocking or interfering with the immunostimulatory activity of LBP has been a therapeutic target of interest.

For example, a polyclonal antibody preparation to murine LBP has been shown to prevent LBP mediated binding of LPS to murine macrophages and subsequent induction of TNF expression in vitro, effectively neutralizing the activity of LBP. This same polyclonal antibody was able to reduce lethality in a murine model of endotoxemia [Gallay et al. (1993), supra].

Several modified forms of LBP have been developed that bind LPS but lack the ability to transfer the LPS molecule to CD14. U.S. application Ser. No. 08/261,660 filed Jun. 17, 1994, now U.S. Pat. No. 5,731,415, hereby incorporated by reference in its entirety, describes novel biologically active polypeptide derivatives of LBP, including LBP derivative hybrid proteins, which are characterized by the ability to bind to LPS and which lack CD14-mediated immunostimulatory properties, including the ability of LBP holoprotein to mediate LPS activity via the CD14 receptor. More particularly, these LBP protein derivatives including LBP derivative hybrid proteins lacking those carboxy terminal-associated elements characteristic of the LBP holoprotein which enable LBP to bind to and interact with the CD14 receptor on monocytes and macrophages so as to provide an immunostimulatory signal to monocytes and macrophages. Such LBP protein derivatives included those characterized by a molecular weight less than or equal to about 25 kD, including an amino-terminal LBP fragment having amino acid residues 1–197 that was designated $rLBP_{25}$. This recombinant protein corresponding to the amino-terminal residues 1–197 of LBP has been shown to bind LPS but could neither facilitate binding of LPS to CD14 nor permit LPS-induced expression of TNF [see also, Theofan et al. (1994), supra; Han et al. (1994), supra]. Additionally, this N-terminal fragment was shown to inhibit LPS-induced expression of TNF that was mediated by full-length LBP [Han et al. (1994), supra]. $rLBP_{25}$ includes amino acid regions comprising LBP residues 17 through 45, 65 through 99 and 141 through 167 which correspond to respective biologically active (e.g., LPS binding) domains (e.g., Domain I—residues 17 through 45; Domain II—residues 65 through 99; and Domain III—residues 142 through 169) of bactericida/permeability-increasing protein (BPI). The LBP derivative hybrid proteins included hybrids of LBP protein sequences with the amino acid sequences of other polypeptides and also characterized by the ability to bind to LPS and the absence of CD14-mediated immunostimulatory properties. Such hybrid proteins included fusions of LBP amino-terminal fragments with polypeptide sequences of other proteins such as BPI, immunoglobulins and the like. Properties of several LBP/BPI fusion proteins have been described by Abrahamson et al., *J. Biol. Chem.* 272(4):2149–2155 (1997). In addition, a recombinant hybrid fusion between the N-terminal 199 amino acid residues of LBP and the C-terminal 257 residues of BPI was shown to be protective in a rodent model of gram-negative sepsis [Opal et al., *Antimicrob. Agents Chemother.* 39(12): 2813–2815 (1995)]. U.S. application Ser. No. 08/261,660 filed Jun. 17, 1994 also describes LBP derivatives in the form of synthetic LBP peptides that are portions of the LBP sequence corresponding to either Domain II (residues 65–99) or Domain III (residues 142–169) of BPI. The LBP derivative designated LBP-1 consisted of residues 73 through 99 of LBP. The LBP derivative designated LBP-2 consisted of residues 140 through 161 of LBP. In addition, Taylor et al., *J. Biol. Chem.* 270(30): 17934–17938 (1995), described synthetic peptides corresponding to residues 91–105 or 94–108 of the mature LBP protein that were reported to compete with LBP for binding to LPS and could inhibit LPS-induced expression of TNF in vitro.

In addition to transferring LPS to CD14, LBP can facilitate the transfer of LPS to serum lipoproteins [Wurfel et al., *J. Exp. Med.* 180: 1025–1035 (1994)]. Association with lipoproteins greatly reduces the inflammatory potential of LPS [Ulevitch and Johnston (1978), supra]. Thus, LBP itself can also participate in the neutralization of LPS. The significance of LBP-mediated transfer of LPS to lipoproteins, however, remains unclear. Specifically, elevated levels of LBP found in acute phase serum have been correlated with a reduction of the rate of association of LPS with lipoproteins [Tobias and Ulevitch, *J. Immunol.* 131(4): 1913–1916 (1983); Tobias et al. (1985), supra; U.S. Pat. Nos. 5,245,013 and 5,310,879]. This ability of LBP to inhibit, rather than facilitate, the transfer of LPS to lipoproteins was exploited in the initial purification of LBP [Tobias et al. (1986), supra].

Dedrick et al., *J. Endotoxin Research* 3(supp. 1):18 (Abstract I-14) (October 1996) reported in an abstract that concentrations of 1 ng/mL to 1 µg/mL of rLBP fully potentiated the induction of TNF expression in serum-free medium by 1 ng/mL LPS on a human monocytic cell line (THP.1). In medium containing 10% serum, LBP concentrations of 30 µg/mL or greater inhibited LPS-induced TNF expression by the THP.1 cells and also inhibited E-selection expression in human umbilical endothelial cells (HUVEC) induced by 10 ng/mL LPS. Moreover, it was reported that administration of 5 mg/kg rLBP also increased survival in mice challenged with up to 25 mg/kg *E. coli* LPS. However, human subjects suffering from disorders involving bacteria and their endotoxin (such as sepsis) have been shown to exhibit substantially elevated levels of LBP in circulation (at concentrations of 50 µg/mL to 100 µg/mL of serum), yet these high circulating levels of LBP do not appear to have inhibited the adverse effects of bacterial endotoxin in circulation that were experienced by these subjects. The role of LBP in promoting or alleviating adverse effects of endotoxin in circulation thus remains unclear.

Bactericidal/permeability-increasing protein (BPI) is a basic protein found in the azurophilic granules of polymorphonuclear leukocytes [Weiss et al., *J. Biol. Chem.* 253(8): 2664–2672 (1978)]. BPI binds to LPS, resulting in its clearance and neutralization. The amino acid sequence of BPI is closely related to that of LBP [Schumann et al. (1990), supra], and like LBP, the amino-terminal half of BPI has a binding site for LPS [Ooi et al., *J. Exp. Med.* 174: 649–655 (1991)]. However, BPI has a higher affinity for LPS than does LBP [Gazzano-Santoro et al., *Infect. Immun.* 62(4): 1185–1191 (1994); Wilde et al., *J. Biol. Chem.* 269(26): 17411–17416 (1994)], and cannot transfer LPS to the CD14 molecule. Thus, BPI effectively competes with LBP for LPS binding [Heumann et al., *J. Infect. Dis.* 167: 1351–1357 (1993); Gazzano-Santoro et al. (1994), supra] and blocks the inflammatory activity of LPS in vitro [Marra et al., *J. Immunol.* 144(2): 662–666 (1990); Ooi et al. (1991), supra], and in humans [de Winter et al., *J. Inflamm.* 45: 193–206 (1995)].

It has been suggested that sCD14 could be a useful therapeutic agent in endotoxin-related disorders [Schütt et al. (1991), supra; Schütt et al. (1992), supra; Haziot et al. (1994), supra; Haziot et al. (1995), supra]. The presence of sCD14 reduces the amount of LPS complexed with LBP [Tobias et al. (1995), supra], because, although LBP has a higher affinity for LPS than sCD14, the distribution of LPS between sCD14 and LBP depends on the molar ratio of the two proteins. sCD14 has been shown to inhibit responses that depend on mCD14 [Schütt et al., *Res. Immunol.* 143: 71–78 (1992); Schütt et al., *Allerg. Immunol.* 37: 159–164 (1991); Haziot et al., *J. Immunol.* 152: 5869–5876 (1994)], and to protect mice against experimental endotoxemia [Haziot, et al., *J. Immunol.* 154: 6529–6532 (1995)].

SUMMARY OF THE INVENTION

The present invention is based on the discovery that lipopolysaccharide binding protein (LBP), an agent previously thought to be stimulatory of the adverse effects of bacteria and their endotoxin, can actually reduce the inflammatory potential of bacteria and their endotoxin when administered to certain subjects prior to exposure to the bacterial endotoxin. In particular, the invention relates to the administration of LBP in an amount effective to inhibit the adverse effects of bacterial endotoxin to a subject who has a circulating level of LBP in the normal range as measured by a quantitative LBP assay. The LBP is administered at a time prior to exposure to bacterial endotoxin (i.e., when the subject will be at risk of such exposure). Such times of "at risk of exposure to endotoxin" include circumstances or conditions associated with increased translocation of gut associated bacteria and endotoxin, particularly prior to surgery. Thus, these subjects are administered prophylactic doses of LBP, to raise the circulating LBP levels to therapeutically effective amounts, in advance of exposure to bacterial endotoxin. The invention thus provides a method of protection against the adverse effects of bacterial endotoxin at a time prior to endotoxin challenge/exposure.

Numerous additional aspects and advantages of the invention will become apparent to those skilled in the art upon consideration of the following detailed description of the invention which describes presently preferred embodiments thereof.

DETAILED DESCRIPTION

Figure 1A:
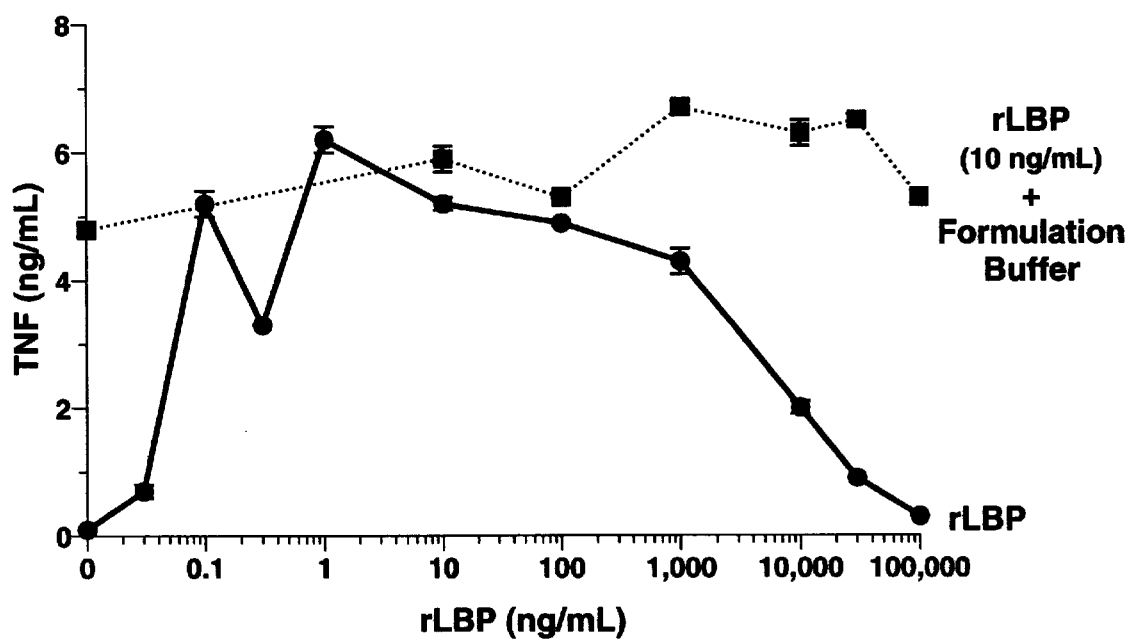
FIGS. 1A and 1B display the effect of varying concentrations of LBP on LPS-induced TNF expression by monocytic THP.1 cells in serum-free and serum-containing medium, respectively.

According to the invention, LBP therapy is specifically useful when prophylactically administered to subjects who have circulating LBP levels in the normal range but who are at risk for exposure to bacterial endotoxin. According to the invention, the LBP levels of the subject may be determined using a sensitive and specific assay, such as described in Example 2 below, and LBP is administered to the subject to increase circulating LBP levels to a prophylactically/therapeutically effective level, for example, from about 15 to about 100 μg/mL, to prevent/inhibit the adverse effects of subsequent exposure to bacterial endotoxin.

Since its identification, LBP has been described as an immunostimulatory molecule, because it potentiates the biological effects of LPS/endotoxin. However, in vitro experiments have demonstrated that the amount of LBP needed to potentiate LPS-induced expression of inflammatory molecules was far below that found in normal human serum. In addition, expression of inflammatory molecules induced by bacterial endotoxin was actually inhibited in vitro when the concentration of LBP was raised above normal circulating concentrations. Furthermore, administration of 5 mg/kg recombinant human LBP to mice following a lethal challenge of endotoxin reduced lethality. Thus, these results suggested that increased levels of circulating rLBP were protective against endotoxin. However, circulating LBP levels have been measured and found to be substantially elevated in human subjects suffering from such disorders involving exposure to bacteria and their endotoxin, such as sepsis, meningococcemia and confirmed abdominal infections. Despite having high circulating levels of LBP (which can rise to greater than 100 μg/mL), these subjects still experienced the adverse effects of bacteria and their endotoxin in circulation.

The present invention is based upon the understanding that increasing LBP levels by administration of LBP protect a subject from the adverse effects of endotoxin exposure if the circulating LBP level is increased before exposure to endotoxin, rather than after exposure to endotoxin.

The present invention specifically contemplates a method for inhibiting adverse effects of endotoxin in circulation, involving determining the circulating lipopolysaccharide binding protein (LBP) level of a subject at risk for exposure to endotoxin, and administering to said subject having a circulating LBP level within the normal range an amount of LBP effective to elevate the circulating LBP level to inhibit the adverse effects of exposure to endotoxin, preferably to a level from about 15 μg/mL to about 100 μg/mL.

Another aspect of the present invention provides compositions comprising lipopolysaccharide binding protein (LBP) in a solution buffered at about pH 7.5 and containing a poloxamer surfactant, and compositions comprising LBP in a solution buffered at about pH 7.5 and containing a poloxamer surfactant and a polysorbate surfactant.

As used herein, "circulating LBP level within the normal range," or "normal circulating LBP level," means, for humans, LBP concentrations in serum or plasma of from about 1 to about 12 μg/mL as measured by the assay described in Example 2 below, using the rLBP of Example 1 as a standard. The normal range may vary depending on the assay and the LBP standards utilized, but can be determined for any assay and LBP standard using a representative population of normal human sera or plasma.

As used herein, "at risk for exposure to endotoxin" include circumstances or conditions, for example, undergoing surgery or surgical procedures including transplantation, that are associated with increased translocation of gut-associated bacteria and their endotoxin.

It is contemplated that polypeptide derivatives of LBP (i.e., fragments of LBP, analogs of LBP in which an amino acid has been deleted, inserted or modified, and fusion proteins comprising LBP) that retain the ability to bind LPS may be administered instead of, or in addition to, LBP, and include derivatives that exhibit CD14-mediated immunostimulatory properties. Such derivatives may be obtained by any synthetic or recombinant means known in the art.

It is contemplated that LBP or derivatives thereof may be administered according to the invention in a pharmaceutical composition with pharmaceutically acceptable diluents, adjuvants, and carriers. A particularly preferred composition of rLBP comprises 1–2 mg/mL LBP in 10 mM HEPES buffer, 150 mM NaCl, pH 7.5 with 0.2% poloxamer 188 and 0.002% polysorbate 80. A preferred composition of $rLBP_{25}$ is similar to that for rLBP except that 1.0 M NaCl instead of 150 mM NaCl is used. According to the invention, LBP or derivatives thereof may be administered systemically and most preferably intravenously in amounts broadly ranging from about 0.1 mg/kg to about 100 mg/kg of body weight of the treated subject, preferably at dosages ranging from about 1 mg/kg to about 25 mg/kg of body weight. Other systemic routes of administration include oral, intravenous, intramuscular or subcutaneous injection (including into a depot for long-term release), intraocular and retrobulbar, intrathecal, intraperitoneal (e.g. by intraperitoneal lavage), intrapulmonary (using powdered drug, or an aerosolized or nebulized drug solution), or transdermal. The treating physician may find it advantageous to continue the prophylactic treatment by continuous infusion or intermittent injection or infusion, at the same, reduced or increased dose per day.

It is further contemplated that LBP or derivatives thereof may be co-administered in conjunction with other agents that bind, clear and/or neutralize endotoxin. "Concurrent administration," or "co-administration," as used herein includes administration of multiple agents, in conjunction or combination, together, or before or after each other. The LBP or derivative and second agent(s) may be administered by different routes, e.g., LBP may be given intravenously while the second agent(s) is(are) administered intramuscularly. The LBP or derivative and second agent(s) may be given sequentially in the same intravenous line or may be given in different intravenous lines. The agents may be administered simultaneously or sequentially, as long as they are given in a manner sufficient to allow all agents to achieve effective concentrations at the site of action.

The present invention further provides a novel use for LBP and fragments or derivatives thereof in the manufacture of medicaments for prophylactically treating subjects at risk of exposure to endotoxin.

Example 1 addresses production and purification of rLBP suitable for use as a therapeutic or for use as a standard in the LBP assay of Example 2. Example 2 addresses a sensitive and specific assay for determining LBP levels in human body fluids. Example 3 addresses in vivo effects of LBP.

EXAMPLE 1

Production and Purification of rLBP

Recombinant LBP (rLBP), suitable for use as a therapeutic according to the invention or for use as a standard in the assay of Example 2 below, was produced and purified as follows. Plasmid pING4539, containing the DNA encoding full length human LBP (amino acids 1–452, designated "rLBP," plus the 25 amino acid signal sequence) [SEQ ID NOS: 1 and 2], was prepared as described in Example 2 of U.S. application Ser. No. 08/261,660 filed Jun. 17, 1994, hereby incorporated by reference in its entirety.

CHO-DG44 cells were transfected with linearized pING4539 DNA (40 µg, digested with PvuI, phenol-chloroform extracted and ethanol precipitated) using electroporation. Following recovery, the cells were diluted and $1 \times 10^4$ cells were plated per 96-well plate well in selective medium consisting of an αMEM medium lacking nucleosides (Irvine Scientific) and supplemented with dialyzed fetal bovine serum (100 mL serum dialyzed against 4 L cold 0.15 NaCl using 6000–8000 cutoff for 16 hours at 4° C.). Untransfected CHO-DG44 cells were unable to grow in this medium because they possess the DHFR⁻ mutation and were removed during successive feedings with the selective medium. At 1.5–2 weeks, microcolonies consisting of transfected cells were observed.

Clones were analyzed for the presence of LBP-reactive protein in culture by ELISA in Immulon-II 96 well plates (Dynatech). Supernatant samples were added to the plates and incubated 46 hours at 4° C., followed by addition of goat anti-LBP antiserum and peroxidase-labeled rabbit anti-goat anti-serum. The 21 most productive positive clones were expanded in selective αMEM medium and then grown in selective medium supplemented with 0.05 µM methotrexate. The best producing amplified clone was chosen based on ELISA of supernatants as described above and then expanded in αMEM media containing 0.05 µM methotrexate for growth in roller bottles.

The transfected CHO-DG44 cells were cultured as follows. All incubations were performed in a humidified 5% $CO_2$ incubator maintained at 37° C. Working stock cultures were grown in DME/F-12 with 10% FCS, and after four days of growth were seeded into five 2-liter roller bottles. After another six days of incubation, these cells were harvested and seeded into 40 2-liter roller bottles using $1 \times 10^7$ cells in 500 mL of DME/F-12 with 5% FCS for each bottle. Four days later, the culture supernatants from each bottle were removed and replaced with 500 mL of fresh DME/F-12 with 2.5% FCS, and 10 mL of an S-Sepharose (Pharmacia) ion exchange resin slurry (50% v/v, sterilized by autoclaving). After four days of incubation, the media containing S-Sepharose was harvested and replaced with fresh media again containing S-Sepharose. This process was repeated one more time, to yield a total of three harvests of S-Sepharose. Each harvest was processed for purification separately until the LBP was eluted from the S-Sepharose beads, and then the three eluates were pooled for the remainder of the purification procedure. Purification methods using S-Sepharose have been described in U.S. Pat. No. 5,439,807, hereby incorporated by reference in its entirety.

All chromatographic resins used in the purification of rLBP were purchased sterile (in ethanol) and equilibrated with pyrogen free buffer or were depyrogenated by immersion in 0.2N NaOH, 1M NaCl and then rinsed with pyrogen-free water followed by equilibration with the appropriate buffer. All buffers and reagents were prepared with bottled, pyrogen-free water for irrigation (Baxter).

After the S-Sepharose beads were harvested from the roller bottles, they were allowed to settle out of the media. The beads were then batch washed with approximately 800 mL of 20 mM MES, pH 6.8, 150 mM NaCl. After washing with approximately 400 mL of 20 mM sodium acetate (NaOAc), pH 4.0, 150 mM NaCl, the beads were loaded into a 2.5×50 cm column. The column was washed with 20 mM NaOAc, pH 4.0, 400 mM NaCl, until the absorbance at 280 nm ($A_{280}$) approached zero, which typically requires approximately 600 mL of buffer. The column was then washed with 20 mM NaOAc, pH 4.0, 600 mM NaCl, again until the $A_{280}$ reading returned to zero, which typically requires about 600 mL of buffer. The rLBP was eluted with 20 mM NaOAc, pH 4.0, 1.0M NaCl. The column was additionally washed with 20 mM NaOAc, 1.5M NaOAc, pH 4.0, 1.5M NaCl to insure all the protein was eluted. Column fractions containing the protein were analyzed by SDS-PAGE, and those containing rLBP were pooled. The pooled fractions were adjusted to a final salt concentration of 200 mM NaCl with 20 mM MES, pH 5.0. This material was then filtered through a 0.2 µm filter.

The pooled filtrate was applied to a 20 mL Q-Sepharose column for removal of nucleic acids and then concentrated on a 20 mL S-Sepharose column equilibrated with 20 mM MES, pH 5.0, 200 mM NaCl. The S-Sepharose column was washed with 20 mM MES, pH 5.0, 400 mM NaCl and again with 20 mM MES, pH 5.0, 550 mM NaCl, using about 200 mL of buffer per wash. The LBP was then eluted with 20 mM MES, pH 5.0, 1.2 M NaCl in about 40 mL of volume. The LBP was buffer exchanged into 10 mM HEPES, pH 7.5, 150 mM NaCl using a 500 mL Sephacryl S-100 column. Fractions were analyzed with SDS-PAGE, and rLBP-containing fractions were pooled. The final protein concentration was adjusted to 1.0 mg/mL and the material was formulated to 0.2% poloxamer 188 (PLURONIC F-68, BASF Wyandotte Corp., Parsippany, N.J.), 0.002% polysorbate 80 (TWEEN 80, ICI Americas, Inc., Wilmington, Del.). The formulated protein was aliquoted for storage and frozen at −70 degrees until use. The yields from this procedure generally range from about 140 mg to about 300 mg rLBP, typically about 200–240 mg rLBP.

EXAMPLE 2

Determination of LBP Levels in Human Plasma and Sera

The ranges of circulating LBP levels for healthy human subjects and for human subjects from a variety of patient populations was determined by assaying representative samples of human plasma or sera with a sandwich ELISA.

The LBP assay was validated by evaluating for interference by other compounds, recovery, precision and clinical sensitivity and specificity. The potential for interference by BPI (which has >45% sequence homology with LBP), LPS, various blood preservatives commonly used in blood collection and heat treatment of blood (to 56° C. or 60° C. to inactivate complement) was investigated. The rLBP prepared as described in Example 1 was used as a standard; the activity of the formulated LBP was shown to be constant over time after storage. rBPI and rBPI$_{23}$ (the recombinant expression product of DNA encoding residues 1 to 199 of BPI) was prepared in the manufacturing facility of XOMA Corporation, Berkeley, Calif. for clinical trials, by a process essentially as described on a smaller scale by Horwitz et al., *Protein Expression and Purification* 8:28–40 (1996).

Affinity-purified rabbit anti-LBP was prepared by procedures well known in the art. Briefly, two rabbits were hyper-immunized with LBP, and pooled antisera from these rabbits was diluted with an equal volume of phosphate buffered saline (PBS), pH 7.2. An LBP-Sepharose column was prepared by coupling rLBP produced and purified as described in Example 1 to cyanogen bromide-activated Sepharose 4B. A portion of the diluted antisera was passed through the LBP-Sepharose column; the column was then washed and bound antibodies were eluted with 0.1M glycine, pH 2.5. Collected fractions were immediately neutralized with 1M sodium phosphate buffer pH 8.0. Peak fractions were identified by measuring absorbance at 280 nm. Several sequential column runs were performed and all peak fractions from each column run were pooled. This pool of affinity-purified rabbit anti-LBP antibody was assigned a lot number and qualified based on consistent performance in the ELISA.

Biotin-labeled rabbit anti-LBP antibody was prepared by procedures well known in the art. Briefly, the antibody was biotin labeled with biotinamidocaproate N-hydroxysuccinimide ester (Sigma) in 0.1M sodium bicarbonate, pH 8.3. Unconjugated biotin was removed and alkaline buffer exchanged by passing the antibody over a PD-10 column (Pharmacia) equilibrated with PBS containing 0.1% sodium azide. This biotin-labeled antibody was assigned a lot number, stored at 2° C. to 8° C., and qualified based on consistent performance in the ELISA.

The sandwich ELISA procedure was carried out as follows. Fifty μL of affinity purified rabbit anti-LBP antibody (2 μg/mL in PBS) was added to each well of Immulon 2 (Dynatech) microtiter plates and incubated overnight at 2–8° C. The antibody solution was removed and 200 μl of 1% non-fat milk (Carnation or equivalent) in PBS was added to all wells. After blocking the plates for 1 hour at room temperature, the wells were washed 3 times with 300 μl/well of wash buffer [PBS/0.05% TWEEN 20 (polysorbate 20, Sigma, St. Louis). Standards, samples and controls were diluted in triplicate with PBS containing 1% bovine serum albumin, 0.05% TWEEN 20 [PBS-BSA/TWEEN] and 10 units/mL of sodium heparin (Sigma), in separate 96-well plates. rLBP standard solutions were prepared as serial two-fold dilutions of concentrations from 100 to 0.012 ng/mL. Each replicate and dilution of the standards, samples and controls (50 μl) was transferred to the blocked microtiter plates and incubated for 1 hour at 37° C.. After the primary incubation, the wells were washed 3 times with 300 μl/well of wash buffer. For each assay, biotin-labeled rabbit anti-LBP antibody was diluted 1/2000 in PBS-BSA/TWEEN and 50 μl was added to all wells. The plates were then incubated for 1 hour at 37° C. All wells were washed 3 times with 300 μl/well of wash buffer. ALkaline phosphatase-labeled streptavidin (Zymed) was diluted 1/2000 in PBS-BSA/TWEEN and 50 μl was added to all wells. After incubation for 15 minutes at 37° C., all wells were washed 3 times with 300 μl/well of wash buffer) and 3 times with 300 μl/well of deionized water and the substrate p-nitrophenylphosphate (1 mg/mL in 10% diethanolamine buffer) was added in a volume of 50 μl to all wells. Color development was allowed to proceed for 1 hour at room temperature, after which 50 μl of 1N NaOH was added to stop the reaction. The absorbance at 405 nm ($A_{405}$) was determined for all wells using a VMAX Plate Reader (Molecular Devices). The mean $A_{405}$ for each set of triplicates was calculated. Outliers (data points deviating more than 20% from the mean) were rejected. A standard curve was plotted at $A_{405}$ versus ng/mL of LBP. The linear range was selected, a computerized (RS/1 Release 4.4.4, Bolt Beranek and Newman, Inc.) linear curve fit was performed, and concentrations were determined for samples and controls by interpolation from the standard curve. Sample curves are visually compared to the standard curve to ensure approximately parallel slopes before data are accepted. Pooled plasma, sera or urine from normal healthy human donors were used as the appropriate "negative" controls. An Assay Control Sample (ACS), prepared by adding rLBP to normal human plasma to a concentration of 50,000 ng/mL, was used as a "positive" control.

Western blot analysis was also performed on selected serum and plasma samples. Briefly, samples were incubated in microtiter wells coated with rabbits anti-LBP that had been prepared and blocked as described above for the sandwich ELISA assay. Six replicate samples were incubated with the rabbit anti-LBP for 1 hour at 37° C. After incubation, LBP was eluted with sample buffer and pooled. Ten μL of eluate from each sample was run on a non-reducing 10% gel under the conditions of Laemmli, *Nature* 227:680–685 (1970). Proteins were transferred to nitrocellulose by standard techniques [Towbin et al., *Proc. Nat'l. Acad. Sci.* 76:4350–4354 (1979)] and probed for immunoreactivity with biotin-labeled rabbit anti-LBP antibody (diluted 1/2000 in 0.25M Tris-HCl, pH 7.2, 0.2M NaCl, 0.3% TWEEN 20) followed by alkaline phosphatase-conjugated streptavidin (diluted 1/2000 in the same buffer). Blots were immersed in a 50 μg/mL solution of 5-bromo-4-chloro-3-indolyl phosphate (Sigma) in 0.12M veronal-acetate buffer, pH 9.8, containing 0.01% (w/v) nitro blue tetrazolium and 4 mM $MgCl_2$. Color development was allowed to proceed for 1 hour at room temperature.

Parameters for the optimization of the LBP sandwich ELISA were evaluated, including signal to noise ratio, the concentration of rabbit anti-LBP and biotin-labeled rabbit anti-LBP antibodies, and curve fit. The optimal concentrations for the rabbit anti-LBP and biotin-labeled rabbit anti-LBP antibodies used in these experiments were 2 μg/mL and a 1:2000 dilution, respectively. The standard curve demonstrated reproducibility with a consistent slope and acceptable signal to noise ratio (>10:1). The linear range for the standard curve was 164–781 pg/mL.

For assay validation, the LBP sandwich ELISA was characterized by determining assay precision, recovery and the least detectable concentration of rLBP. These parameters were investigated by performing the sandwich ELISA on human plasma spiked with different concentrations of rLBP and then frozen and thawed to mimic the processing of clinical samples.

Assay precision was expressed as the coefficient of variation for LBP values of the assay control sample (ACS) and normal human plasma (NHP) measured more than 40 times. The mean and standard deviation for ACS and NHP were 39,300±7,930 ng/mL and 2,970±349 ng/mL, respectively. The CV for the ACS and NHP were 20% and 12%, respectively. A more recent evaluation of assay precision produced comparable values for ACS and NHP of 43,220±8543 ng/mL (CV 19.8% ) and 4,372±315 ng/mL (CV 7.2%), respectively. The NHP values are consistent with the endogenous levels of LBP in normal human sera reported by Letureq et al., *J. Cell. Biochem.*, Suppl. 16C:161 (1992) which ranged from 1 to 24 μg/mL, with an average of 7 μg/mL. Acceptance of assay data is based on the ACS values obtained with each assay.

Average recovery of LBP spiked into human plasma (defined as the amount of rLBP measured in spiked samples minus the concentration in the unspiked control, divided by the actual amount spiked in the sample) was 68% across a rLBP concentration range of 0 to 168,000 ng/mL. Average recovery of LBP spiked into human urine was 77% over an rLBP range of 3 to 1000 ng/mL. The lowest detectable concentration of LBP spiked into human plasma (producing a discernible signal above background) was 0.164 ng/mL.

Western blot data clearly demonstrated that the sandwich ELISA is specific for LBP. When plasma samples from normal and presumed septic patients were evaluated, all patient samples exhibited a single 60 kD band similar to the LBP controls. In the sandwich ELISA, LBP levels for these patients ranged from 3.35 to 113 μg/mL.

The sandwich ELISA was also performed on blood samples that had been heat-treated to 56° C. or 60° C.. Heat treatment diminished the amount of LBP detected (compared to sera maintained at 4° C.) by 34% and 97%, respectively.

For the interference studies, the sandwich ELISA and Western blot analysis were performed on donor blood samples collected in tubes containing acid-citrate-dextrose (ACD), ethylene-diaminetetraacetic acid (EDTA) or heparin, and on control samples of donor blood collected without preservatives and control samples of commercially available normal human serum. Blood preservatives did not interfere with the detection of LBP using the sandwich ELISA. Results obtained using the same blood collected with and without preservatives were comparable. Western blot analysis revealed a band pattern that was the same as the pattern for the LBP controls or for commercially available normal human sera.

The sandwich ELISA and Western blot analysis were also performed on samples spiked with varying concentrations of rBPI and rBPI$_{23}$. Because heparin minimizes non-specific adsorption of BPI to the microtiter plate (see U.S. Pat. Nos. 5,466,580 and 5,466,581, both of which are hereby incorporated by reference in their entirety), heparin was added to assay diluents in order to minimize the signal generated by BPI in the sandwich ELISA. The results of these analyses showed that this sandwich ELISA does not demonstrate significant cross-reactivity with BPI. The affinity purified rabbit anti-LBP was not cross-reactive with either rBPI or rBPI$_{23}$ on Western blot analysis. In the sandwich ELISA, the reactivity of BPI and rBPI$_{23}$ at concentrations ranging from 0.78 to 100 ng/mL was comparable to background level, but higher concentrations of both forms of BPI (greater than 100 ng/mL) demonstrated some cross-reactivity.

In addition, the ability of LPS to interfere with detection of LBP in the sandwich ELISA was evaluated. No interference by LPS was observed; addition of LPS (at concentrations ranging from 0 to 100 ng/mL) to samples spiked with varying concentrations (7, 16 and 168 μg/mL) of LBP did not diminish the amount of LBP detected in the ELISA.

These data confirm that the LBP sandwich ELISA described is specific for LBP. The standard curve for the assay is consistent and reproducible, and the assay can detect concentrations of LBP as low as 164 pg/mL.

This assay was used to determine LBP levels in normal human subjects and in a variety of patient populations. See U.S. Pat. No. 5,484,705 and U.S. Ser. No. 08/377,391 filed Jan. 24, 1995, now U.S. Pat. No. 5,804,367 both of which are hereby incorporated by reference in their entirety. Plasma or sera samples from healthy human subjects and humans from a variety of patient populations, including rheumatoid arthritis (RA), acute graft vs. host disease after bone marrow transplantation (BM aGvHD), acute lymphocytic leukemia (ALL), chronic lymphocytic leukemia (CLL), cutaneous T-cell lymphoma (CTCL), diabetes, psoriasis, scleroderma, sepsis, abdominal infection, meningococcemia, Crohn's disease, aplastic anemia (AA), systemic lupus erythematosus (SLE), acute immunodeficiency syndrome (AIDS), alcoholic fatty liver, alcoholic hepatitis, alcoholic cirrhosis, ulcerative colitis and non-alcoholic cirrhosis, were assayed as described above. Results are shown below in Table 1. Results for each of the 59 samples from the healthy human population are displayed in Table 2 below. Of these 59 samples, 58 samples had LBP levels ranging from 1.43 μg/mL to 7.70 μ/mL, while one sample had an LBP level of 11.20 μg/mL.

TABLE 1

| POPULATION | No. of Subjects | Mean μg/mL LBP in Plasma or Sera | Std. Dev. | Std. Error |
|---|---|---|---|---|
| HEALTHY | 59 | 4.1 | 1.7 | 0.2 |
| SEPSIS | 390 | 30.6 | 17.6 | 0.9 |
| ABDOMINAL INFECTION | 16 | 52.1 | 23.9 | 6.2 |
| MENINGOCOCCEMIA | 17 | 19.7 | 9.5 | 2.4 |
| RA | 86 | 7.8 | 4.8 | 0.5 |
| BM aGvHD | 8 | 9.1 | 5.6 | 2.0 |
| ALL | 6 | 8.7 | 8.1 | 3.3 |
| CLL | 9 | 7.7 | 5.1 | 1.7 |
| CTCL | 12 | 7.5 | 4.2 | 1.2 |
| DIABETES | 13 | 2.8 | 1.2 | 0.3 |
| PSORIASIS | 13 | 8.2 | 4.0 | 1.1 |
| SCLERODERMA | 4 | 7.2 | 2.9 | 1.5 |
| CROHN'S | 19 | 16.1 | 10.2 | 2.4 |
| APLASTIC ANEMIA | 16 | 9.5 | 9.2 | 2.3 |
| SLE | 10 | 6.7 | 2.4 | 0.8 |
| AIDS | 15 | 5.3 | 2.3 | 0.6 |
| ALCOHOLIC FATTY LIVER | 10 | 8.5 | 7.0 | 2.2 |
| ALCOHOLIC HEPATITIS | 9 | 8.0 | 4.8 | 1.6 |
| ALCOHOLIC CIRRHOSIS | 11 | 10.9 | 4.6 | 1.4 |
| ULCERATIVE COLITIS | 7 | 21.0 | 19.8 | 7.5 |
| NON-ALCOHOLIC CIRRHOSIS | 6 | 10.7 | 8.4 | 3.4 |

TABLE 2

LBP Levels in Plasma/Sera Samples of 59 Healthy Human Subjects

| μg/mL LBP | μg/mL LBP | μg/mL LBP | μg/mL LBP |
|---|---|---|---|
| 2.59 | 5.09 | 4.57 | 3.50 |
| 2.75 | 5.11 | 4.13 | 6.40 |
| 2.86 | 5.77 | 4.11 | 7.70 |
| 2.93 | 5.95 | 4.00 | 3.60 |
| 3.19 | 5.99 | 4.09 | 3.60 |
| 3.26 | 7.41 | 1.52 | 1.70 |
| 3.64 | 11.20 | 3.01 | 3.40 |
| 3.67 | 3.70 | 2.93 | 4.00 |

TABLE 2-continued

LBP Levels in Plasma/Sera Samples of 59 Healthy Human Subjects

| µg/mL LBP | µg/mL LBP | µg/mL LBP | µg/mL LBP |
|---|---|---|---|
| 3.95 | 2.01 | 3.62 | 3.50 |
| 3.96 | 1.99 | 6.20 | 2.40 |
| 4.37 | 1.43 | 2.78 | 6.60 |
| 4.41 | 2.78 | 3.60 | 5.60 |
| 4.42 | 3.62 | 4.20 | 5.30 |
| 4.91 | 2.35 | 4.10 | 4.40 |
| 4.98 | 2.94 | 3.20 | |

EXAMPLE 3

In Vivo Effect of LBP

The following is an exemplary procedure for administration of LBP according to the invention. A human subject, for example, a patient about to undergo a surgical procedure, is identified as a subject at risk for exposure to endotoxin. An LBP assay such as the assay described above in Example 2 is performed on plasma or serum from the subject to determine the subject's circulating LBP level. If the subject's circulating LBP level is normal, then the subject is treated with an LBP composition such as that described above in Example 1 at an appropriate time before surgery as determined by the treating physician, e.g., from 0–24 hours prior to surgery, preferably prior to induction of anesthesia, and more preferably from 1–2 hours prior to surgery. The LBP composition is administered parenterally, e.g., intravenously, and the circulating prophylactic/therapeutic LBP level after such administration may be confirmed by a second LBP assay on plasma or serum from the patient.

Figure 1B:
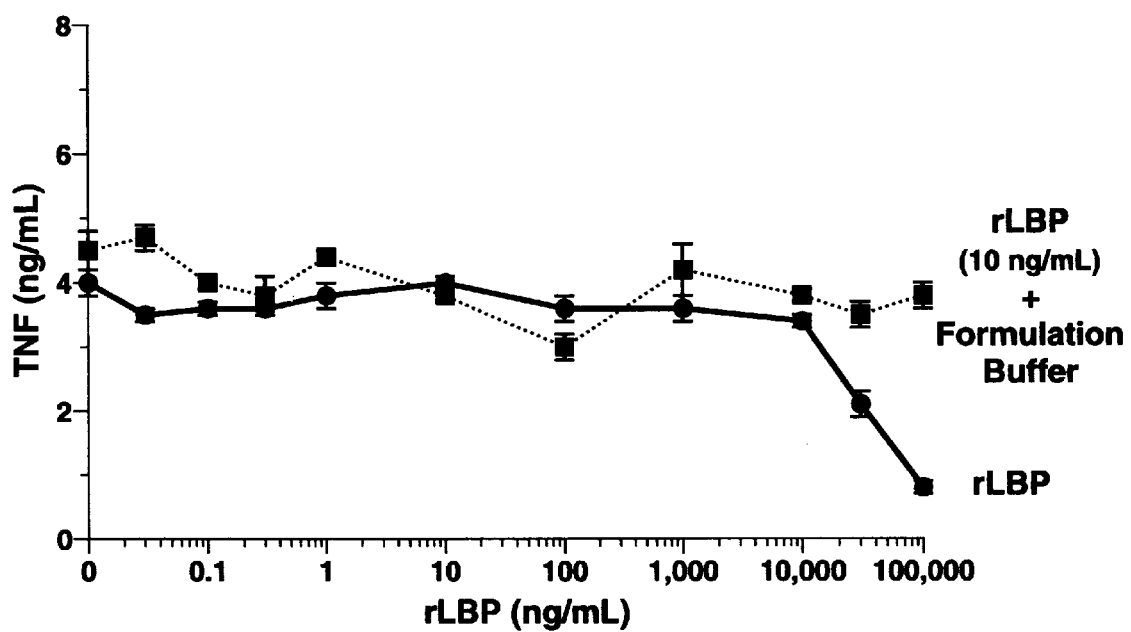

In a separate, related experiment, the effect of LBP on LPS-induced TNF Expression in a monocytic cell line (THP.1) was evaluated as follows. THP.1 cells were maintained in RPMI (GibcoBRL, Gaithersburg, Md.) with 10% fetal bovine serum (FBS) and were cultured in RPMI with 10% FBS plus 50 ng/mL 1,25-dihydroxy-vitamin D (BIOMOL Research Laboratories Inc, Plymouth Meeting, Pa.) for three days prior to treatment with LPS to induce CD14 expression. Before incubation with LPS, cells were washed three times with RPMI and suspended in either RPMI with 10% FBS or in serum free medium [RPMI supplemented with 1% HB101 (Irvine Scientific, Santa Ana, Calif.)]. Cells ($5 \times 10^4$/well) were added to 96 well plates. Aliquots of rLBP, diluted in the same medium as the cells, were added to final concentrations of from 0 to 100,000 ng/mL. Expression of TNF was induced by the addition of E. coli O128 LPS (Sigma, St. Louis, Mo.) to a final concentration of 1 ng/mL. Plates were incubated for 3 hours at 37° C. in 5% $CO_2$, then an aliquot of the supernatant was removed and assayed for TNF by the WEHI 164 toxicity assay using CellTiter 96™ $AQ_{ueous}$ (Promega Corp., Madison, Wis.) to monitor cell viability. Results displayed in FIG. 1A showed that mCD14-dependent induction of TNF expression by 1 ng/mL LPS in THP. 1 cells in serum-free medium was potentiated by low levels of rLBP (<1 µg/mL) but was inhibited by high levels of rLBP (>10 µg/mL) in vitro. Results displayed in FIG. 1B showed that the LPS-induced TNF expression in medium with 10% serum was inhibited by 30 µg/mL and 100 µg/mL rLBP.

Figure 2A:
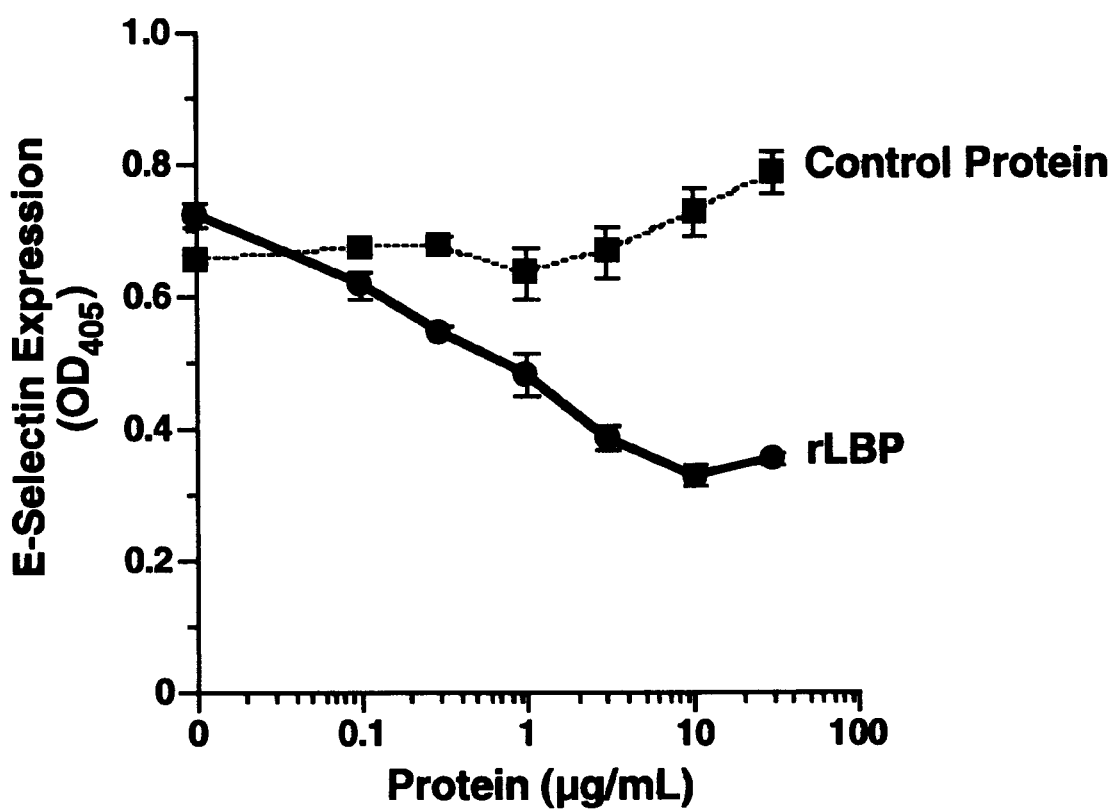
FIGS. 2A and 2B display the effect of varying concentrations of LBP on E-selectin expression by HUVEC induced by LPS and 1L-1β, respectively.
Figure 2B:
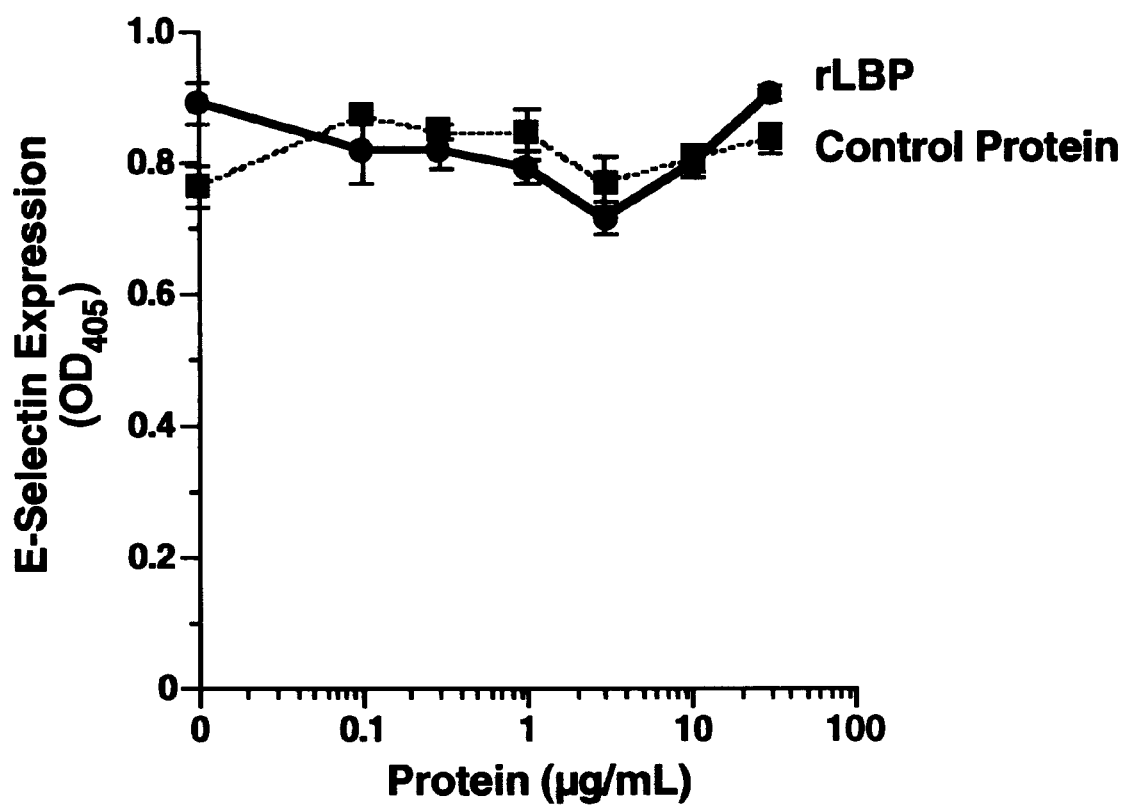

In another separate, related experiment, the effect of LBP on E-selectin expression in human umbilical vein endothelial cells (HUVEC) was also evaluated as follows. HUVEC (Clonetics, San Diego, Calif.) were maintained in endothelial cell growth medium (EGM, Clonetics) with 5% FBS. Cells were grown to confluence in 96 well plates, washed, and medium containing rLBP was added to fmal concentrations of from 0 to 50 µg/mL rLBP. The cells were incubated with 10 ng/mL E. coli O128 LPS or 10 pg/mL IL-1β (Genzyme) for 4 hours in M199 (GibcoBRL) with 10% FBS. Cell surface E-selectin expression was measured by ELISA as described in Huang et al., *Inflammation* 19:389–404 (1995), and is displayed in FIGS. 2A and 2B. High levels of rLBP inhibited sCD14-dependent induction of E-selectin by LPS, but not by 1L-1β.

Figure 3A:
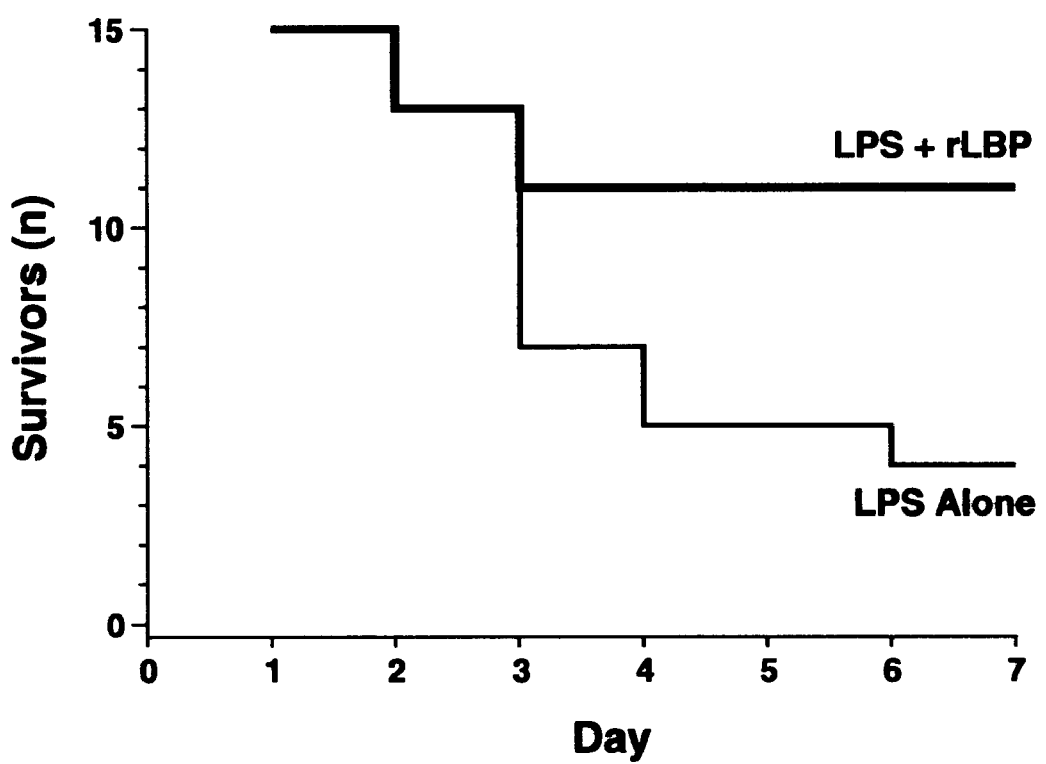
FIGS. 3A, 3B and 3C display the effect of 5 mg/kg LBP on survival of mice administered lethal doses of 15, 20 and 25 mg/kg LPS, respectively.
Figure 3B:
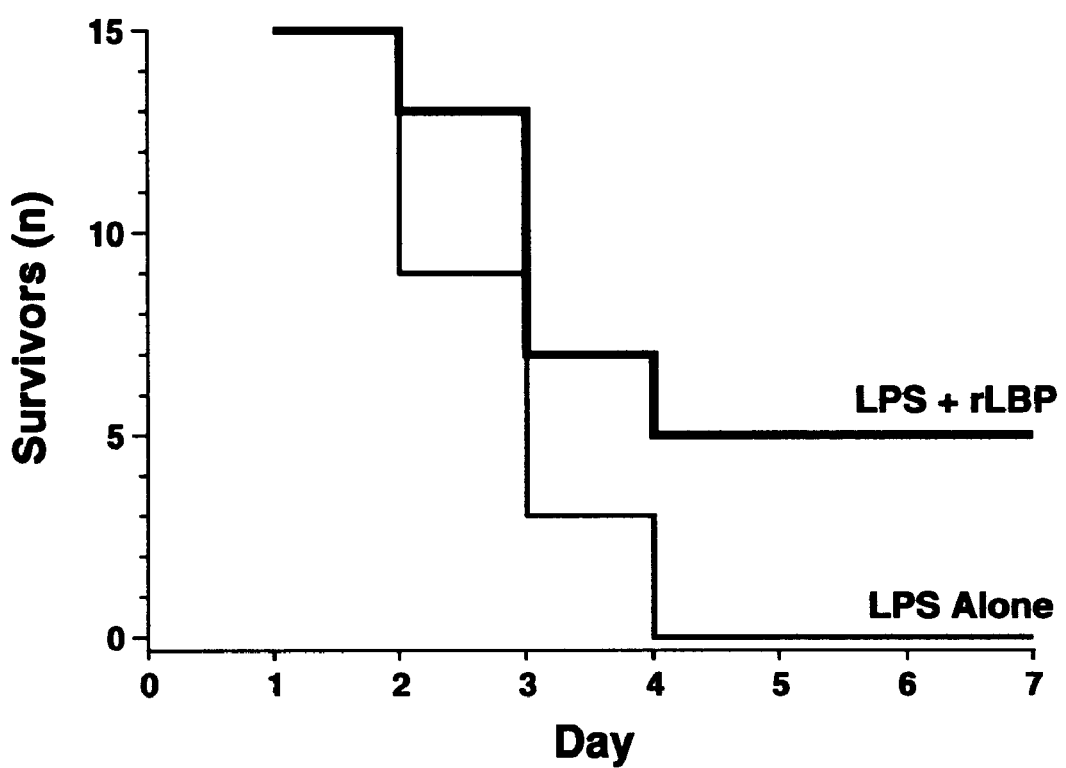
Figure 3C:
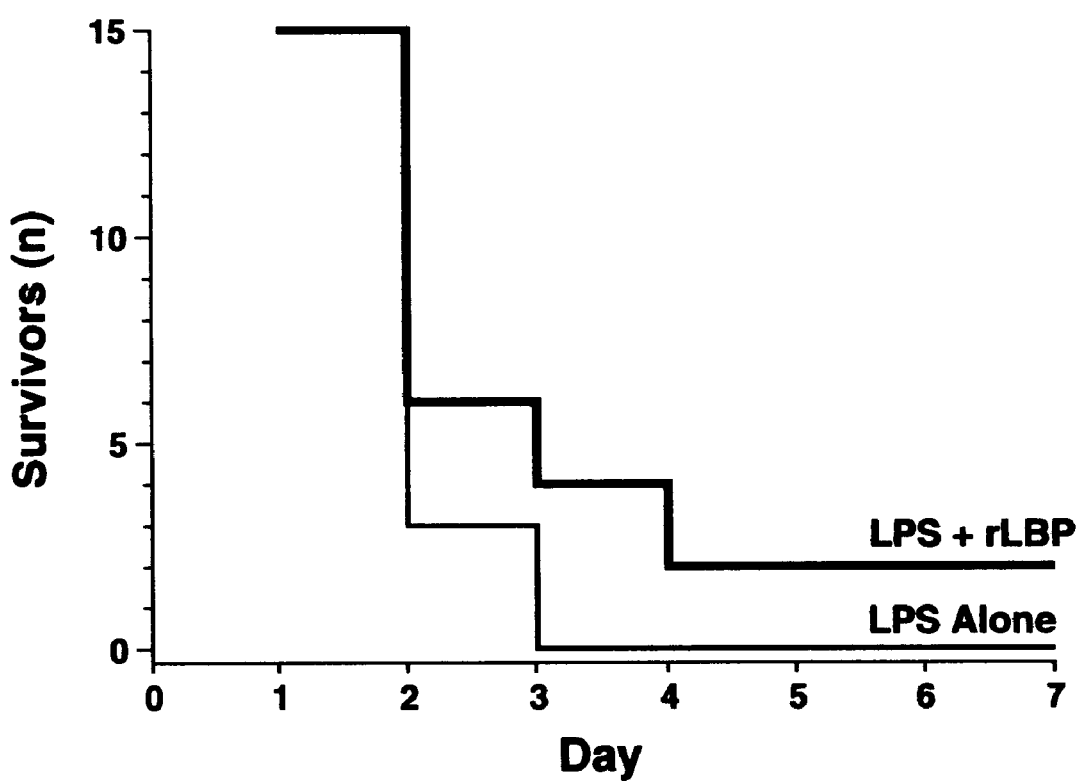

In yet a further separate, related experiment, the effect of LBP injected following endotoxin challenge on survival in an mouse model of lethal endotoxemia was evaluated as follows. CD1 mice (n=15 per group). were challenged intravenously with 15, 20, 25 mg/kg E. coli O111:B4 LPS (Sigma) and then immediately treated intravenously with 5 mg/kg rLBP or vehicle (rLBP formulation buffer). Mortality was recorded for 7 days and is displayed in FIGS. 3A, 3B and 3C. The results show that administration of 5 mg/kg rLBP to these mice was protective following lethal endotoxin doses of 15 and 20 mg/kg (p<0.05 vs. LPS alone).

Numerous modifications and variations in the practice of the invention are expected to occur to those skilled in the art upon consideration of the foregoing description of the presently preferred embodiments thereof. Consequently, the only limitations which should be placed upon the scope of the present invention are those which appear in the appended claims.

What is claimed is:

1. A method for prophylactic treatment against adverse effects of endotoxin in circulation comprising the steps of
   determining the circulating lipopolysaccharide binding protein (LBP) level of a subject at risk for exposure to endotoxin, and, before exposure of the subject to endotoxin,
   administering to said subject having a circulating LBP level within the normal range an amount of LBP effective to elevate the circulating LBP level to inhibit the adverse effects of exposure to endotoxin.

2. The method of claim 1 wherein the circulating LBP level of said subject is elevated to a level from about 15 μg/mL to about 100 μg/mL.

3. The method of claim 1 wherein the circulating LBP level of said subject continues to be elevated at the time of exposure to endotoxin.

* * * * *

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
      (A) LENGTH: 1443 base pairs
      (B) TYPE: nucleic acid
      (C) STRANDEDNESS: single
      (D) TOPOLOGY: linear (ii) MOLECULE TYPE: DNA (ix) FEATURE:

(A) NAME/KEY: CDS
(B) LOCATION: 1..1443

(ix) FEATURE:
(A) NAME/KEY: mat_peptide
(B) LOCATION: 76..1443

(ix) FEATURE:
(A) NAME/KEY: misc_feature
(D) OTHER INFORMATION: "rLBP"

(xi) SEQUENCE DESCRIPTION: SEQ ID NO:1:

```
ATG GGG GCC TTG GCC AGA GCC CTG CCG TCC ATA CTG CTG GCA TTG CTG        48
Met Gly Ala Leu Ala Arg Ala Leu Pro Ser Ile Leu Leu Ala Leu Leu
-25                 -20                 -15                 -10

CTT ACG TCC ACC CCA GAG GCT CTG GGT GCC AAC CCC GGC TTG GTC GCC        96
Leu Thr Ser Thr Pro Glu Ala Leu Gly Ala Asn Pro Gly Leu Val Ala
            -5                   1                   5

AGG ATC ACC GAC AAG GGA CTG CAG TAT GCG GCC CAG GAG GGG CTA TTG       144
Arg Ile Thr Asp Lys Gly Leu Gln Tyr Ala Ala Gln Glu Gly Leu Leu
         10                  15                  20

GCT CTG CAG AGT GAG CTG CTC AGG ATC ACG CTG CCT GAC TTC ACC GGG       192
Ala Leu Gln Ser Glu Leu Leu Arg Ile Thr Leu Pro Asp Phe Thr Gly
     25                  30                  35

GAC TTG AGG ATC CCC CAC GTC GGC CGT GGG CGC TAT GAG TTC CAC AGC       240
Asp Leu Arg Ile Pro His Val Gly Arg Gly Arg Tyr Glu Phe His Ser
 40                  45                  50                  55

CTG AAC ATC CAC AGC TGT GAG CTG CTT CAC TCT GCG CTG AGG CCT GTC       288
Leu Asn Ile His Ser Cys Glu Leu Leu His Ser Ala Leu Arg Pro Val
                 60                  65                  70

CCT GGC CAG GGC CTG AGT CTC AGC ATC TCC GAC TCC TCC ATC CGG GTC       336
Pro Gly Gln Gly Leu Ser Leu Ser Ile Ser Asp Ser Ser Ile Arg Val
             75                  80                  85

CAG GGC AGG TGG AAG GTG CGC AAG TCA TTC TTC AAA CTA CAG GGC TCC       384
Gln Gly Arg Trp Lys Val Arg Lys Ser Phe Phe Lys Leu Gln Gly Ser
         90                  95                 100

TTT GAT GTC AGT GTC AAG GGC ATC AGC ATT TCG GTC AAC CTC CTG TTG       432
Phe Asp Val Ser Val Lys Gly Ile Ser Ile Ser Val Asn Leu Leu Leu
    105                 110                 115

GGC AGC GAG TCC TCC GGG AGG CCC ACA GTT ACT GCC TCC AGC TGC AGC       480
Gly Ser Glu Ser Ser Gly Arg Pro Thr Val Thr Ala Ser Ser Cys Ser
120                 125                 130                 135

AGT GAC ATC GCT GAC GTG GAG GTG GAC ATG TCG GGA GAC TTG GGG TGG       528
Ser Asp Ile Ala Asp Val Glu Val Asp Met Ser Gly Asp Leu Gly Trp
                140                 145                 150

CTG TTG AAC CTC TTC CAC AAC CAG ATT GAG TCC AAG TTC CAG AAA GTA       576
Leu Leu Asn Leu Phe His Asn Gln Ile Glu Ser Lys Phe Gln Lys Val
            155                 160                 165

CTG GAG AGC AGG ATT TGC GAA ATG ATC CAG AAA TCG GTG TCC TCC GAT       624
Leu Glu Ser Arg Ile Cys Glu Met Ile Gln Lys Ser Val Ser Ser Asp
        170                 175                 180

CTA CAG CCT TAT CTC CAA ACT CTG CCA GTT ACA ACA GAG ATT GAC AGT       672
Leu Gln Pro Tyr Leu Gln Thr Leu Pro Val Thr Thr Glu Ile Asp Ser
    185                 190                 195

TTC GCC GAC ATT GAT TAT AGC TTA GTG GAA GCC CCT CGG GCA ACA GCC       720
Phe Ala Asp Ile Asp Tyr Ser Leu Val Glu Ala Pro Arg Ala Thr Ala
200                 205                 210                 215

CAG ATG CTG GAG GTG ATG TTT AAG GGT GAA ATC TTT CAT CGT AAC CAC       768
Gln Met Leu Glu Val Met Phe Lys Gly Glu Ile Phe His Arg Asn His
                220                 225                 230

CGT TCT CCA GTT ACC CTC CTT GCT GCA GTC ATG AGC CTT CCT GAG GAA       816
Arg Ser Pro Val Thr Leu Leu Ala Ala Val Met Ser Leu Pro Glu Glu
            235                 240                 245
```

```
CAC AAC AAA ATG GTC TAC TTT GCC ATC TCG GAT TAT GTC TTC AAC ACG        864
His Asn Lys Met Val Tyr Phe Ala Ile Ser Asp Tyr Val Phe Asn Thr
        250                 255                 260

GCC AGC CTG GTT TAT CAT GAG GAA GGA TAT CTG AAC TTC TCC ATC ACA        912
Ala Ser Leu Val Tyr His Glu Glu Gly Tyr Leu Asn Phe Ser Ile Thr
265                 270                 275

GAT GAG ATG ATA CCG CCT GAC TCT AAT ATC CGA CTG ACC ACC AAG TCC        960
Asp Glu Met Ile Pro Pro Asp Ser Asn Ile Arg Leu Thr Thr Lys Ser
280                 285                 290                 295

TTC CGA CCC TTC GTC CCA CGG TTA GCC AGG CTC TAC CCC AAC ATG AAC       1008
Phe Arg Pro Phe Val Pro Arg Leu Ala Arg Leu Tyr Pro Asn Met Asn
                300                 305                 310

CTG GAA CTC CAG GGA TCA GTG CCC TCT GCT CCG CTC CTG AAC TTC AGC       1056
Leu Glu Leu Gln Gly Ser Val Pro Ser Ala Pro Leu Leu Asn Phe Ser
            315                 320                 325

CCT GGG AAT CTG TCT GTG GAC CCC TAT ATG GAG ATA GAT GCC TTT GTG       1104
Pro Gly Asn Leu Ser Val Asp Pro Tyr Met Glu Ile Asp Ala Phe Val
        330                 335                 340

CTC CTG CCC AGC TCC AGC AAG GAG CCT GTC TTC CGG CTC AGT GTG GCC       1152
Leu Leu Pro Ser Ser Ser Lys Glu Pro Val Phe Arg Leu Ser Val Ala
    345                 350                 355

ACT AAT GTG TCC GCC ACC TTG ACC TTC AAT ACC AGC AAG ATC ACT GGG       1200
Thr Asn Val Ser Ala Thr Leu Thr Phe Asn Thr Ser Lys Ile Thr Gly
360                 365                 370                 375

TTC CTG AAG CCA GGA AAG GTA AAA GTG GAA CTG AAA GAA TCC AAA GTT       1248
Phe Leu Lys Pro Gly Lys Val Lys Val Glu Leu Lys Glu Ser Lys Val
                380                 385                 390

GGA CTA TTC AAT GCA GAG CTG TTG GAA GCG CTC CTC AAC TAT TAC ATC       1296
Gly Leu Phe Asn Ala Glu Leu Leu Glu Ala Leu Leu Asn Tyr Tyr Ile
            395                 400                 405

CTT AAC ACC TTC TAC CCC AAG TTC AAT GAT AAG TTG GCC GAA GGC TTC       1344
Leu Asn Thr Phe Tyr Pro Lys Phe Asn Asp Lys Leu Ala Glu Gly Phe
        410                 415                 420

CCC CTT CCT CTG CTG AAG CGT GTT CAG CTC TAC GAC CTT GGG CTG CAG       1392
Pro Leu Pro Leu Leu Lys Arg Val Gln Leu Tyr Asp Leu Gly Leu Gln
    425                 430                 435

ATC CAT AAG GAC TTC CTG TTC TTG GGT GCC AAT GTC CAA TAC ATG AGA       1440
Ile His Lys Asp Phe Leu Phe Leu Gly Ala Asn Val Gln Tyr Met Arg
440                 445                 450                 455

GTT                                                                   1443
Val (2) INFORMATION FOR SEQ ID NO:2:

(i) SEQUENCE CHARACTERISTICS:
        (A) LENGTH: 481 amino acids
        (B) TYPE: amino acid
        (D) TOPOLOGY: linear (ii) MOLECULE TYPE: protein (ix) FEATURE:
        (A) NAME/KEY: misc_feature
        (D) OTHER INFORMATION: "rLBP"

(xi) SEQUENCE DESCRIPTION: SEQ ID NO:2:

Met Gly Ala Leu Ala Arg Ala Leu Pro Ser Ile Leu Leu Ala Leu Leu
-25                 -20                 -15                 -10

Leu Thr Ser Thr Pro Glu Ala Leu Gly Ala Asn Pro Gly Leu Val Ala
                -5                   1                   5

Arg Ile Thr Asp Lys Gly Leu Gln Tyr Ala Ala Gln Glu Gly Leu Leu
            10                  15                  20
```

```
Ala Leu Gln Ser Glu Leu Leu Arg Ile Thr Leu Pro Asp Phe Thr Gly
             25                  30                  35

Asp Leu Arg Ile Pro His Val Gly Arg Gly Arg Tyr Glu Phe His Ser
 40                  45                  50                  55

Leu Asn Ile His Ser Cys Glu Leu Leu His Ser Ala Leu Arg Pro Val
                 60                  65                  70

Pro Gly Gln Gly Leu Ser Leu Ser Ile Ser Asp Ser Ser Ile Arg Val
                 75                  80                  85

Gln Gly Arg Trp Lys Val Arg Lys Ser Phe Phe Lys Leu Gln Gly Ser
             90                  95                 100

Phe Asp Val Ser Val Lys Gly Ile Ser Ile Ser Val Asn Leu Leu Leu
            105                 110                 115

Gly Ser Glu Ser Ser Gly Arg Pro Thr Val Thr Ala Ser Ser Cys Ser
120                 125                 130                 135

Ser Asp Ile Ala Asp Val Glu Val Asp Met Ser Gly Asp Leu Gly Trp
                140                 145                 150

Leu Leu Asn Leu Phe His Asn Gln Ile Glu Ser Lys Phe Gln Lys Val
            155                 160                 165

Leu Glu Ser Arg Ile Cys Glu Met Ile Gln Lys Ser Val Ser Ser Asp
            170                 175                 180

Leu Gln Pro Tyr Leu Gln Thr Leu Pro Val Thr Thr Glu Ile Asp Ser
185                 190                 195

Phe Ala Asp Ile Asp Tyr Ser Leu Val Glu Ala Pro Arg Ala Thr Ala
200                 205                 210                 215

Gln Met Leu Glu Val Met Phe Lys Gly Glu Ile Phe His Arg Asn His
                220                 225                 230

Arg Ser Pro Val Thr Leu Leu Ala Ala Val Met Ser Leu Pro Glu Glu
                235                 240                 245

His Asn Lys Met Val Tyr Phe Ala Ile Ser Asp Tyr Val Phe Asn Thr
            250                 255                 260

Ala Ser Leu Val Tyr His Glu Glu Gly Tyr Leu Asn Phe Ser Ile Thr
            265                 270                 275

Asp Glu Met Ile Pro Pro Asp Ser Asn Ile Arg Leu Thr Thr Lys Ser
280                 285                 290                 295

Phe Arg Pro Phe Val Pro Arg Leu Ala Arg Leu Tyr Pro Asn Met Asn
                300                 305                 310

Leu Glu Leu Gln Gly Ser Val Pro Ser Ala Pro Leu Leu Asn Phe Ser
            315                 320                 325

Pro Gly Asn Leu Ser Val Asp Pro Tyr Met Glu Ile Asp Ala Phe Val
            330                 335                 340

Leu Leu Pro Ser Ser Ser Lys Glu Pro Val Phe Arg Leu Ser Val Ala
345                 350                 355

Thr Asn Val Ser Ala Thr Leu Thr Phe Asn Thr Ser Lys Ile Thr Gly
360                 365                 370                 375

Phe Leu Lys Pro Gly Lys Val Lys Val Glu Leu Lys Glu Ser Lys Val
                380                 385                 390

Gly Leu Phe Asn Ala Glu Leu Leu Glu Ala Leu Leu Asn Tyr Tyr Ile
            395                 400                 405

Leu Asn Thr Phe Tyr Pro Lys Phe Asn Asp Lys Leu Ala Glu Gly Phe
            410                 415                 420

Pro Leu Pro Leu Leu Lys Arg Val Gln Leu Tyr Asp Leu Gly Leu Gln
425                 430                 435

Ile His Lys Asp Phe Leu Phe Leu Gly Ala Asn Val Gln Tyr Met Arg
```

| 440 | 445 | 450 | 455 |
|---|---|---|---|
| Val | | | |